(12) United States Patent
Knodel et al.

(10) Patent No.: US 8,556,935 B1
(45) Date of Patent: Oct. 15, 2013

(54) METHOD OF MANUFACTURING SURGICAL STAPLES

(75) Inventors: Bryan D. Knodel, Flagstaff, AZ (US); Philipe R. Manoux, Oakland, CA (US)

(73) Assignee: Cardica, Inc., Redwood City, CA (US)

( * ) Notice: Subject to any disclaimer, the term of this patent is extended or adjusted under 35 U.S.C. 154(b) by 393 days.

(21) Appl. No.: 13/048,778

(22) Filed: Mar. 15, 2011

(51) Int. Cl.
*A61B 17/068* (2006.01)

(52) U.S. Cl.
USPC ............. 606/219; 606/139; 606/153; 227/19; 227/175.1; 227/176.1

(58) Field of Classification Search
USPC .............. 227/19, 175.1, 176.1, 178.1, 180.1; 606/139, 143, 151, 153, 158, 219; 29/243.56
See application file for complete search history.

(56) References Cited

U.S. PATENT DOCUMENTS

| | | | |
|---|---|---|---|
| 3,581,551 A | 6/1971 | Wilkinson | |
| 3,650,453 A | 3/1972 | Smith, Jr. | |
| 3,899,914 A | 8/1975 | Akiyama | |
| 4,086,926 A | 5/1978 | Green et al. | |
| 4,228,895 A | 10/1980 | Larkin | |
| 4,475,679 A | 10/1984 | Fleury, Jr. | |
| 4,633,861 A | 1/1987 | Chow et al. | |
| 4,762,260 A | 8/1988 | Richards et al. | |
| 4,969,591 A | 11/1990 | Richards et al. | |
| 5,156,315 A | 10/1992 | Green et al. | |
| 5,192,288 A | 3/1993 | Thompson et al. | |
| 5,413,272 A | 5/1995 | Green et al. | |
| 5,441,509 A * | 8/1995 | Vidal et al. ................ 606/151 |
| 5,476,206 A | 12/1995 | Green | |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,855,311 A | 1/1999 | Hamblin et al. | |
| 5,894,979 A | 4/1999 | Powell | |

(Continued)

FOREIGN PATENT DOCUMENTS

| EP | 1238634 | 9/1994 |
|---|---|---|
| JP | 2005160933 | 6/2005 |

(Continued)

OTHER PUBLICATIONS

Gong, Shao W., "Perfectly flexible mechanism and integrated mechanism system design", *Mechanism and Machine Theory* 39 (2004), (Nov. 2004),1155-1174.

(Continued)

*Primary Examiner* — Scott A. Smith
(74) *Attorney, Agent, or Firm* — Cardica, Inc.

(57) ABSTRACT

One exemplary process for manufacturing a surgical apparatus may include providing a flat, generally-planar strip of biocompatible material; cutting the strip to produce a feeder belt with at least one lateral edge, and staples affixed to the feeder belt in proximity to at least one lateral edge, where the staples and feeder belt are substantially aligned along a first plane; and bending at least one staple out of the first plane, while the feeder belt remains in the first plane. Another exemplary process for manufacturing a surgical apparatus may include providing a flat, generally-planar strip of biocompatible material; cutting that strip to produce a feeder belt with edges, and staples affixed to different edges of the feeder belt; and coining at least one staple after the cutting.

20 Claims, 5 Drawing Sheets

(56) References Cited

U.S. PATENT DOCUMENTS

| | | | |
|---|---|---|---|
| 5,918,791 | A | 7/1999 | Sorrentino et al. |
| 5,964,774 | A | 10/1999 | McKean et al. |
| 6,306,149 | B1 | 10/2001 | Meade |
| 6,391,038 | B2 | 5/2002 | Vargas et al. |
| 6,602,252 | B2 | 8/2003 | Mollenauer |
| 6,716,232 | B1 | 4/2004 | Vidal et al. |
| 6,817,508 | B1 | 11/2004 | Racenet |
| 6,843,403 | B2 | 1/2005 | Whitman |
| 6,994,714 | B2 * | 2/2006 | Vargas et al. ................ 606/153 |
| 7,025,747 | B2 | 4/2006 | Smith |
| 7,097,089 | B2 | 8/2006 | Marczyk |
| 7,140,527 | B2 | 11/2006 | Ehrenfels et al. |
| 7,168,604 | B2 | 1/2007 | Milliman et al. |
| 7,172,104 | B2 | 2/2007 | Scirica et al. |
| 7,179,267 | B2 | 2/2007 | Nolan et al. |
| 7,207,471 | B2 | 4/2007 | Heinrich et al. |
| 7,213,736 | B2 | 5/2007 | Wales et al. |
| 7,225,963 | B2 | 6/2007 | Scirica |
| 7,225,964 | B2 | 6/2007 | Mastri et al. |
| 7,234,624 | B2 | 6/2007 | Gresham et al. |
| 7,238,195 | B2 | 7/2007 | Viola |
| 7,954,683 | B1 * | 6/2011 | Knodel et al. ............. 227/175.1 |
| 7,988,026 | B2 * | 8/2011 | Knodel et al. ............. 227/175.1 |
| 8,056,789 | B1 * | 11/2011 | White et al. ............... 227/180.1 |
| 8,070,036 | B1 * | 12/2011 | Knodel ...................... 227/178.1 |
| 8,240,538 | B1 * | 8/2012 | Manoux ..................... 227/178.1 |
| 8,261,958 | B1 * | 9/2012 | Knodel ...................... 227/176.1 |
| 8,317,072 | B1 * | 11/2012 | Knodel et al. ............. 227/175.1 |
| 8,365,973 | B1 * | 2/2013 | White et al. ............... 227/176.1 |
| 8,397,973 | B1 * | 3/2013 | Hausen ...................... 227/176.1 |
| 8,403,956 | B1 * | 3/2013 | Thompson et al. .......... 606/219 |
| 2003/0120284 | A1 | 6/2003 | Palacios et al. |
| 2003/0236551 | A1 | 12/2003 | Peterson |
| 2005/0184121 | A1 | 8/2005 | Heinrich |
| 2006/0011699 | A1 | 1/2006 | Olson et al. |
| 2006/0041273 | A1 | 2/2006 | Ortiz et al. |
| 2006/0151567 | A1 | 7/2006 | Roy |
| 2007/0027472 | A1 | 2/2007 | Hiles et al. |
| 2007/0034668 | A1 | 2/2007 | Holsten et al. |
| 2007/0073341 | A1 | 3/2007 | Smith et al. |
| 2007/0083234 | A1 | 4/2007 | Shelton, IV et al. |
| 2007/0118163 | A1 | 5/2007 | Boudreaux et al. |
| 2007/0125828 | A1 | 6/2007 | Rethy et al. |
| 2008/0078807 | A1 | 4/2008 | Hess et al. |
| 2009/0065552 | A1 | 3/2009 | Knodel et al. |

FOREIGN PATENT DOCUMENTS

| | | |
|---|---|---|
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory* 38, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg.* 60(3), (Mar. 1973),191-197.

"Notification of Transmittal of the International Search Report and the Written Opinion of the International Searching Authority", PCT/US2008/075449, (Apr. 29, 2009).

"International Search Report", PCT/US2008/075449, (Apr. 29, 2009).

"Written Opinion of the International Searching Authority", PCT/US2008/075449, (Apr. 29, 2009).

"Cardica Microcutter Implant Delivery Device 510(k), Cover Sheet, Table 10.1, "Substantial Equivalence Comparison," and Section 12, "Substantial Equivalence Discussion"".

* cited by examiner

US 8,556,935 B1

METHOD OF MANUFACTURING SURGICAL STAPLES

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. The surgeon inserts the endocutter through a trocar or other port or incision in the body, orients the end of the endocutter around the tissue to be transected, and compresses the anvil and cartridge together to clamp the tissue. Then, a row or rows of staples are deployed on either side of the transection line, and a blade is advanced along the transection line to divide the tissue.

During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter. That inconvenience may discourage surgeons from using the endocutter for procedures in which use of an endocutter may benefit the patient.

BRIEF DESCRIPTION OF THE DRAWINGS

The use of the same reference symbols in different figures indicates similar or identical items.

DETAILED DESCRIPTION

Figure 1:
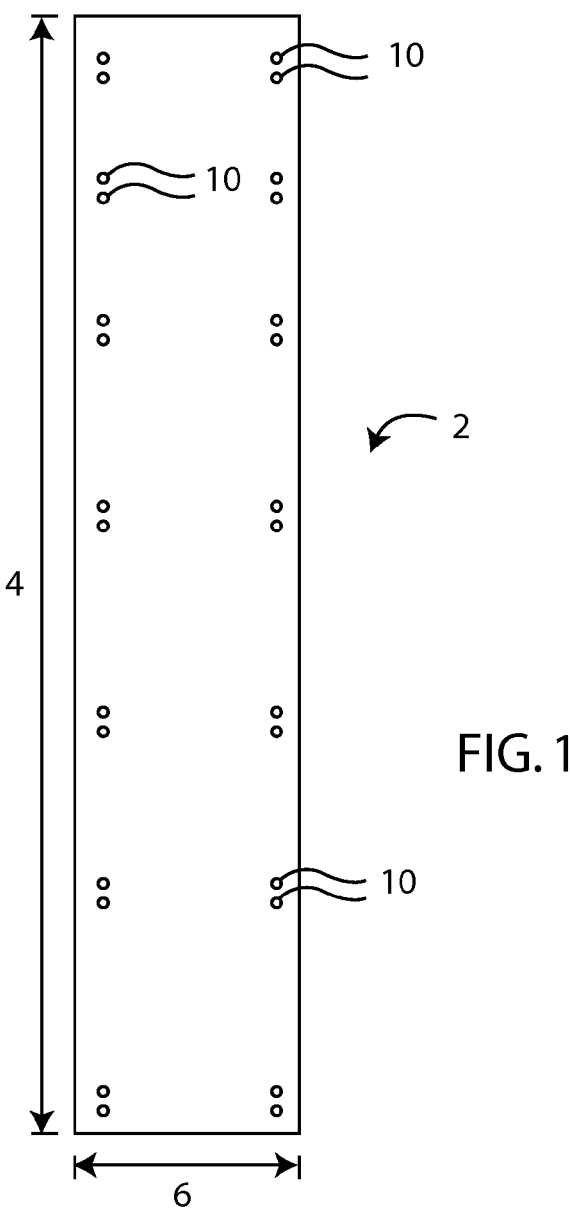
FIG. 1 is a top view of a blank strip.
Figure 2:
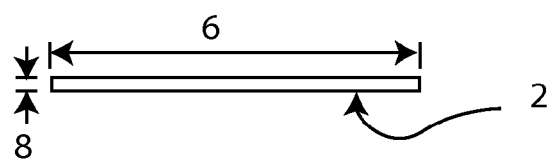
FIG. 2 is a side view of the blank strip of FIG. 1.

Referring to FIGS. 1-2, a blank strip 2 is shown. The strip 2 has a length 4, width 6 and height 8. Advantageously, the strip 2 may be longer than illustrated in FIG. 1; the particular length illustrated is chosen for convenience in description. The strip 2 may be substantially flat and generally planar, at least in the particular area to be worked as described below. As used in this document, the term "generally planar" refers to a strip 2 with a width 6 and length 4 substantially greater than its height 8. Alternately, the strip 2 need not be generally planar, in whole or in part. Optionally, a remainder of the strip 2 located away from the particular area to be worked as described below may be stored in a reel, for compactness of storage and for ease of feeding the blank 2 into stamps, progressive dies or the like. One or more alignment apertures 10 may be defined through the strip 2 to ensure registration of the strip 2 to the machine or machines that act upon the strip 2. Advantageously, the blank 2 has substantially the same height 8 along its length 4. Alternately, the blank 2 may vary in height 8 along its length 4.

The strip 2 may be composed of any suitable material that is biocompatible. As one example, the strip 2 may be 316L stainless steel. As another example, the strip 2 may be a different stainless steel alloy. As another example, the strip 2 may be titanium or a titanium alloy. As another example, the strip 2 may be a polymer such as polyglycolic acid. As another example, the strip 2 may be a resorbable material that gradually dissolves inside the human body. Providing a strip 2 may be a first action 30 in a manufacturing process 40.

The strip 2 may be acted upon by one or more tools to create a finished set of staples affixed to a staple strip. As one example, the strip 2 may be stamped by a set of progressive dies in one or more presses, at one or more stations. As another example, one or more of such stations may include a step other than or in addition to stamping, such as laser-cutting. As another example, the strip 2 may be acted on by one or more tools, none of which are a die or stamp. For purposes of clarity and brevity, the progressive stamping of the strip 2 is described herein. A feeding system may push the strip 2 through stations of a progressive stamping die. Each station may perform one or more operations, as described below.

Figure 3:
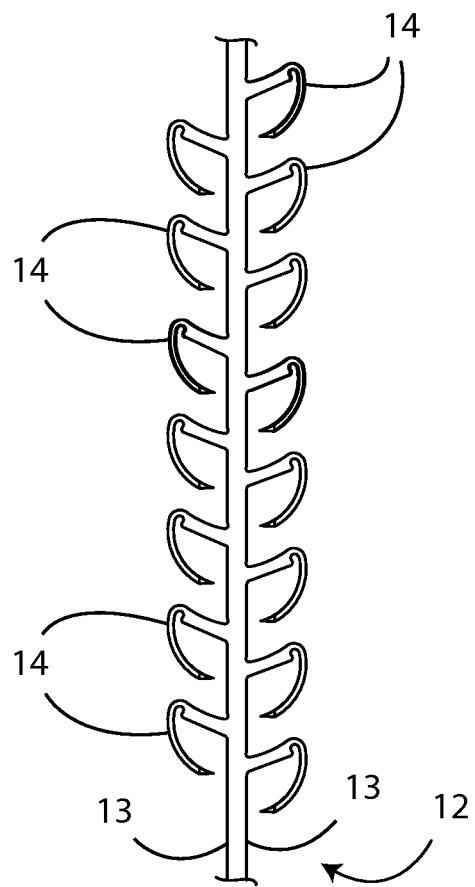
FIG. 3 is a top view of staples affixed to a feeder belt, produced by cutting the blank strip of FIGS. 1-2.
Figure 7:
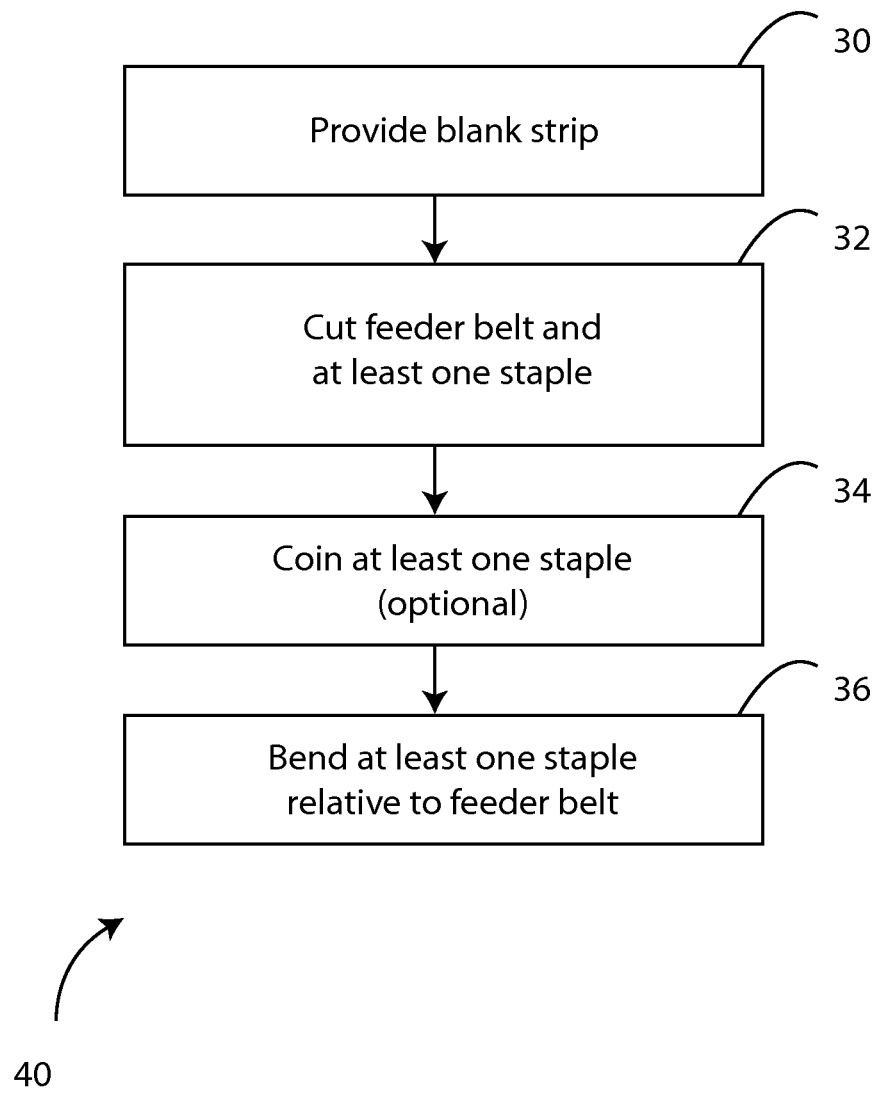
FIG. 7 is a flow chart illustrating a method for manufacturing staples affixed to a feeder belt.

First, referring also to FIGS. 3 and 7, at least a segment of the strip 2 is cut to produce a feeder belt 12 integral with and affixed to staples 14, in a second action 32 in a manufacturing process 40. The feeder belt 12 and staples 14 may be configured substantially as set forth in U.S. Patent Application Publication No. 2009/0065552, published on Mar. 12, 2009, which is herein incorporated by reference in its entirety. As one example, at least a segment of the strip 2 is fed into a first stamping station, and the strip 2 is stamped one or more times to remove excess material and result in the unitary, flat combination of the feeder belt 12 and staples 14 shown in FIG. 3. The staples 14 may be generally U-shaped, generally V-shaped, or may have any other suitable shape. The staples 14 may be homogeneous in shape, or one or more staples 14 may be shaped differently from one or more other staples 14. The feeder belt 12 may have two laterally-spaced edges 13, where one or more staples 14 extend from one or both of those edges 13 of the feeder belt 12. Where the strip 2 is stamped more than once to form the feeder belt 12 and staples 14, the strip 2 may be advanced to a different station for one or more of those additional stampings. The apertures 10 in the strip 2 may be used to register the strip 2 to each station to ensure that the stamping operation at that particular station is performed on the proper specific part of the strip 2. Registration of the strip 2 to a stamping station using apertures 10 in the strip 2 is standard in the progressive stamping art. Four separate stampings with four separate dies may be used to produce the feeder belt 12 and staples 14 of FIG. 3. Alternately, any suitable number of dies and/or stampings may be used to produce the feeder belt 12 and staples 14. At the end of the cutting operation, the feeder belt 12 and staples 14 are a single part, lying substantially in the plane previously occupied by the strip 2 as a whole. Further, the staples 14 and/or feeder belt 12 may remain affixed to a portion of the strip 2, such as a portion extending laterally outward from the staples 14. In this way, the apertures 10 in the strip 2 still can be used to register the feeder belt 12 and staples 14 to the next station, and the strip 2 can be used to move the feeder belt 12 and staples 14 to the next station. That portion of the strip 2 is not shown in FIG. 3, for clarity.

Figure 4:
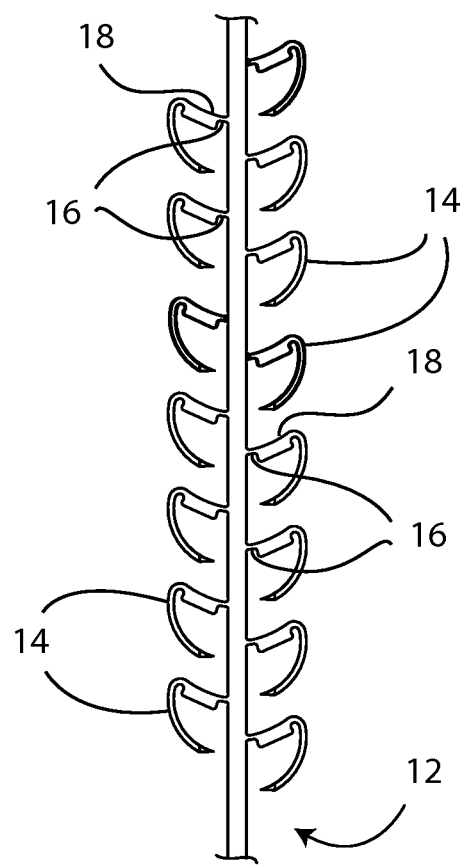
FIG. 4 is a top view of the staples and feeder belt of FIG. 3, after staples have been coined.

Next, referring also to FIG. 4, optionally one or more of the staples 14 may be coined in a third action 34 in a manufacturing process 40. "Coining" refers to a form of stamping in which a workpiece is subjected to a sufficiently high stress to induce plastic flow on the surface of the material. The plastic flow may work-harden the area coined, while the area not coined retains its toughness and ductility. Coining compresses an area of a part through plastic flow, rather than cutting. Where one or more of the staples 14 is coined, that staple or staples 14 are coined at and/or near the junction between an end of each staple 14 and the feeder belt 12, resulting in a narrow area 16 at and/or near the end of each staple 14 that is affixed to the feeder belt 12. The narrowness of the narrow area 16 compared to the width of the adjacent portion of the leg 18 affixed to the feeder belt 12 focuses bending of the staple 14 at the narrow area 16 during deployment, and facilitates shearing of the staple 14 from the feeder belt 12 at the narrow area 16 during deployment. The deployment process of a staple 14, and the bending and breaking off of the staple 14 from the feeder belt 12 during that deployment process, may be substantially as set forth in U.S. Patent Application Publication No. 2009/0065552. As one example, the strip 2 is fed into a stamping station in which coining is performed, separate from the first stamping station in which cutting is performed. Two separate stamping operations, with one or more separate dies, may be used to coin one or more staples 14 to form a narrow area 16 on each such coined staple 14. Alternately, a different number of stamping operations or dies may be used. As another example, the feeder belt 12 may be coined adjacent to the connection between the feeder belt 12 and one or more staples 14, instead of or in addition to coining such staples 14.

Figure 5:
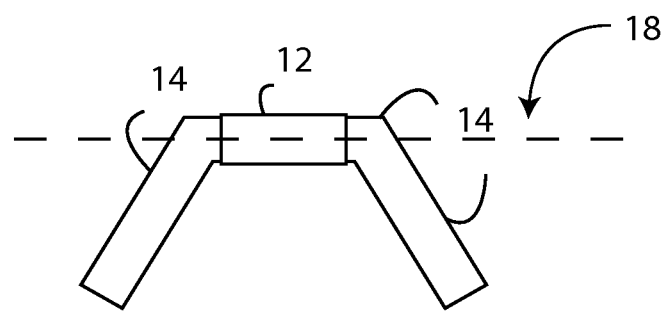
FIG. 5 is an end view of the staples and feeder belt of FIGS. 3-4, as staples are bent out of plane relative to the feeder belt.
Figure 6:
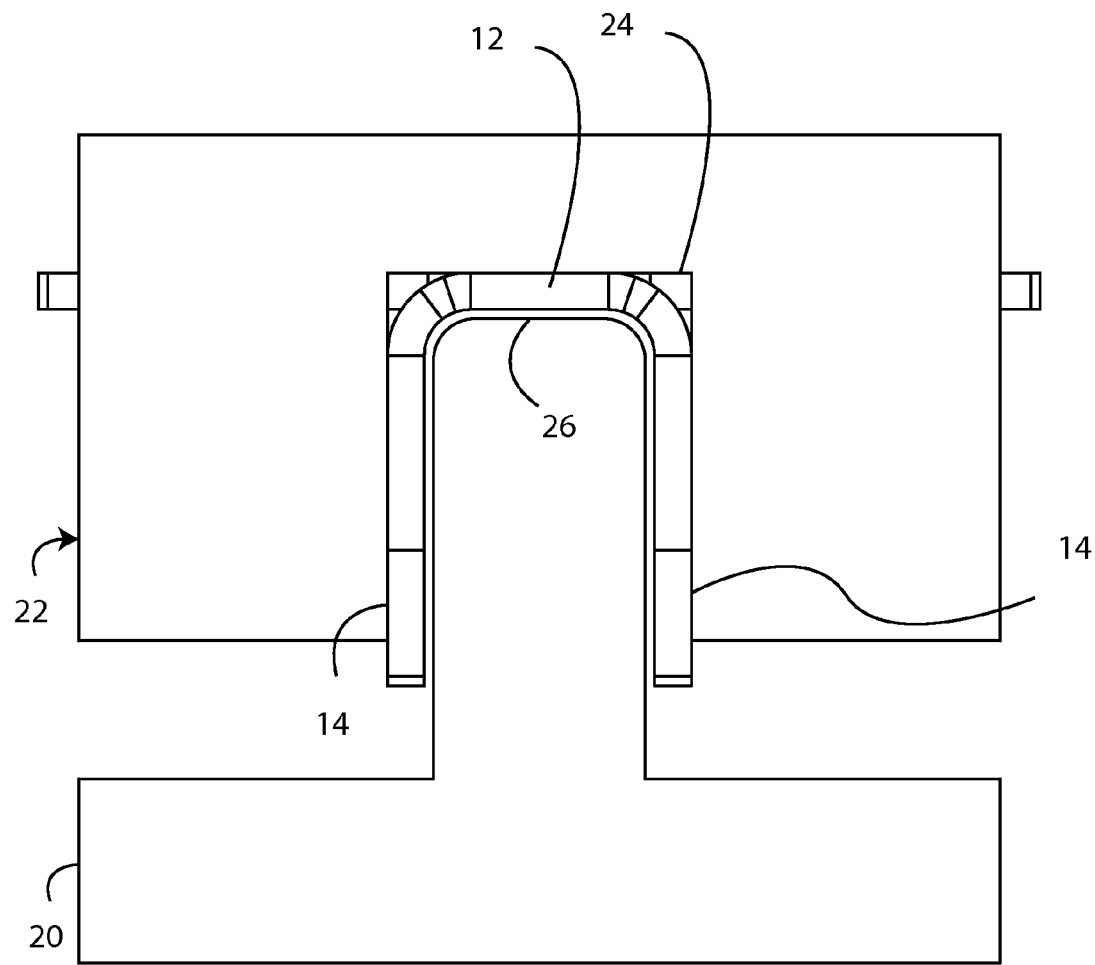
FIG. 6 is a schematic view of a stamp usable to bend staples relative to the feeder belt.

Next, referring also to FIGS. 5-6, at least one staple 14 may be bent out of plane relative to the feeder belt 12 in an action 36 in a manufacturing process 40. As one example, the strip 2 is fed into a stamping station in which bending is performed, separate from the stamping station or stations in which cutting is performed, and separate from the stamping station or stations in which coining is performed, where coining is performed on one or more staples 14. The feeder belt 12 may generally define a plane 18, as described above, where that plane 18 may generally bisect the feeder belt 12 into generally-identical upper and lower halves. After the cutting operation described above, and the coining operation if such coining operation is performed, the staples 14 may be substantially aligned along the same plane 18 as the feeder belt 12, as seen in FIGS. 3-4. At least one staple 14 may be bent out of plane 18 relative to the feeder belt 12 to any appropriate angle. As seen in FIG. 6, at least one staple 14 may be bent at an angle of substantially 90 degrees relative to the feeder belt 12. As another example, one or more staples 14 may be bent to any other suitable non-zero angle relative to the feeder belt 12. Referring to FIG. 6, as an example of bending, a first die 20 may hold the feeder belt 12, and a second die 22 may be positioned above the feeder belt 12. The first die 20 may have an inverted T-shape as viewed on end, and the second die 22 may include a trench 24 or other opening defined therein as viewed on end. The feeder belt 12 may be placed on the platform 26 that defines the upper surface of the first die 20, at the top of the inverted T shape. In order to bend one or more staples 14 out of plane relative to the feeder belt 12, the second die 22 may be moved toward the first die 20, which may be fixed. As another example, the first die 20 may be moved toward the second die 22, which may be fixed. As another example, the first die 20 and the second die 22 may be moved toward one another. Referring also to FIG. 5, as the bottom of the second die 22 adjacent to the rectangular trench moves downward relative to the first die 20, it contacts and bends downward at least one staple 14. As the second die 22 continues to move downward, it continues to bend one or more staples 14. Referring to FIG. 6, after the second die 22 has stopped moving downward, one or more of the staples 14 have been bent to a final angle relative to the feeder belt 12, in which the feeder belt 12 remains in its original, first plane, and at least one staple 14 is aligned along a second plane different from the first plane. At this time, one or more of the staples 14 may be positioned against the inner surface of the trench 24. The trench 24, and the upwardly-extending portion of the first die 20, may be sized and shaped such that, in the final position of the dies 20, 22, the trench 24 and the upwardly-extending portion of the first die 20 may be spaced apart from one another a distance slightly greater than the thickness of a staple 14. A single stamping operation may be used to bend one or more staples 14 out of plane relative to the feeder belt 12. As another example, two or more stamping operations, with one or more separate dies, may be used to bend one or more staples 14 out of plane relative to the feeder belt 12.

At this point, the progressive stamping process is complete. Optionally, the strip 2 may be advanced, and returned to the first stamping station at which cutting is performed. The steps of cutting, optionally coining, and bending the staples 14 may be repeated on a portion of the strip 2 that was not previously stamped. If so, the portion of the strip 2 that has been stamped may be cut from the remainder of the strip 2, depending on the length of the strip 2 that has been stamped and the desired length of a finished feeder belt 12. This cutting of the portion of the strip 2 that has been stamped may be a standard cutoff operation as utilized as a final step in progressive stamping.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A process for manufacturing a surgical apparatus, comprising:
   providing a flat, generally-planar strip of biocompatible material;
   cutting said strip to produce a feeder belt with at least one lateral edge, and a plurality of staples affixed to said feeder belt in proximity to at least one said lateral edge, said staples and said feeder belt substantially aligned along a first plane; and bending at least one said staple out of said first plane, while said feeder belt remains in said first plane.

2. Surgical apparatus manufactured by the process of claim 1.

3. The process of claim 1, wherein said biocompatible material is stainless steel.

4. The process of claim 1, wherein said biocompatible material is a titanium alloy.

5. The process of claim 1, further comprising coining at least one said staple after said cutting and before said bending.

6. The process of claim 1, wherein said cutting is performed by stamping said flat strip.

7. The process of claim 1, wherein said bending is performed by stamping said feeder belt and said staples.

8. The process of claim 1, wherein said bending comprises bending at least one said staple to form substantially a right angle between said at least one staple and said feeder belt.

9. A process for manufacturing a surgical apparatus, comprising:
providing a flat, generally-planar strip of biocompatible material;
cutting said strip to produce a feeder belt with a plurality of edges, and a plurality of staples affixed to different said edges of said feeder belt; and
coining at least one said staple after said cutting.

10. The process of claim 9, wherein said cutting produces a plurality of staples extending from each of two laterally-opposed edges of said feeder belt.

11. The process of claim 9, wherein said biocompatible material is stainless steel.

12. The process of claim 9, wherein each of said cutting, said coining and said bending are performed by stamping.

13. The process of claim 9, further comprising bending at least one said staple relative to said feeder belt after said coining.

14. The process of claim 13, wherein said bending comprises bending at least one said staple to form approximately a right angle between said at least one staple and said feeder belt.

15. A process for manufacturing a surgical apparatus, comprising:
providing a flat, generally-planar strip of biocompatible material;
stamping said strip to cut a feeder belt with at least one lateral edge, and cut a plurality of staples affixed to said feeder belt in proximity to said lateral edge, said staples and said feeder belt substantially aligned along a first plane; and
stamping at least one of said feeder belt and said staples to coin at least one said staple after said stamping said strip to cut a feeder belt; and
stamping at least one said staple to bend said at least one staple out of said first plane, while said feeder belt remains in said first plane.

16. The process of claim 15, wherein said biocompatible material is stainless steel.

17. The process of claim 15, wherein said stamping said strip to cut a feeder belt with at least one lateral edge, and cut a plurality of staples affixed to said feeder belt, includes cutting at least one staple with two spaced-apart ends, one of which is affixed to said feeder belt and one of which is free.

18. The process of claim 15, further comprising moving said strip, then repeating each of said stamping actions on a portion of said strip that was not previously stamped.

19. The process of claim 15, wherein at least one said staple is generally V-shaped.

20. The process of claim 15, wherein at least one said staple is generally U-shaped.

* * * * *